(12) United States Patent
Emig et al.

(10) Patent No.: US 8,008,324 B2
(45) Date of Patent: *Aug. 30, 2011

(54) INDOLE DERIVATIVES AND THEIR USE AS MEDICAMENT

(75) Inventors: Peter Emig, Bruchkobel (DE); Gerald Bacher, Gemering (DE); Dietmar Reichert, Eschau (DE); Silke Basner, Schoneck (DE); Beate Aue, Grobostheim/Ringheim (DE); Bernd Nickel, Muhltal (DE); Eckhard Gunther, Maintal (DE)

(73) Assignee: AEterna Zentaris GmbH, Frankfurt/Main (DE)

( * ) Notice: Subject to any disclaimer, the term of this patent is extended or adjusted under 35 U.S.C. 154(b) by 47 days.

This patent is subject to a terminal disclaimer.

(21) Appl. No.: 12/074,845

(22) Filed: Mar. 6, 2008

(65) Prior Publication Data

US 2008/0153875 A1 Jun. 26, 2008

Related U.S. Application Data

(60) Continuation of application No. 12/004,168, filed on Dec. 20, 2007, now Pat. No. 7,989,453, which is a division of application No. 09/910,140, filed on Jul. 20, 2001, now Pat. No. 7,365,081.

(30) Foreign Application Priority Data

Jul. 28, 2000 (DE) .................................. 100 37 310

(51) Int. Cl.
*A61K 31/67* (2006.01)
*A61K 31/445* (2006.01)
*C07D 215/38* (2006.01)
*C07D 215/36* (2006.01)
*C07D 401/06* (2006.01)

(52) U.S. Cl. ........ 514/314; 514/313; 514/331; 546/162; 546/171; 546/277.1

(58) Field of Classification Search .................. 514/313, 514/314, 331; 546/162, 171, 277.1
See application file for complete search history.

(56) References Cited

U.S. PATENT DOCUMENTS

| | | | |
|---|---|---|---|
| 3,573,294 A | 3/1971 | Lang et al. | |
| 5,965,582 A | 10/1999 | Lebaut et al. | |
| 6,008,231 A | 12/1999 | Lebaut et al. | |
| 6,232,327 B1 | 5/2001 | Nickel et al. | |
| 6,344,467 B1 | 2/2002 | Lebaut et al. | |
| 6,432,987 B2 | 8/2002 | Gunther et al. | |
| 6,693,119 B2 | 2/2004 | Nickel et al. | |
| 6,706,722 B2 | 3/2004 | Emig et al. | |
| 6,987,122 B2 | 1/2006 | Menta et al. | |
| 7,365,081 B2 * | 4/2008 | Emig et al. ..................... | 514/314 |

FOREIGN PATENT DOCUMENTS

| | | |
|---|---|---|
| CA | 2326833 | 10/1999 |
| DE | 19814838 | 10/1999 |
| EP | 490 263 A1 | 6/1992 |
| FR | 3 632 M | 10/1965 |
| HU | P0101530 | 11/2001 |
| WO | WO 97/22619 | 6/1997 |
| WO | WO 98/00946 | 1/1998 |
| WO | WO 98/09946 A | 3/1998 |
| WO | WO 98/09946 A1 | 3/1998 |
| WO | WO 99/43654 | 9/1999 |
| WO | WO 99/46267 | 9/1999 |
| WO | WO 99/51224 | 10/1999 |
| WO | WO 99/51224 A | 10/1999 |
| WO | WO 99/51224 A1 | 10/1999 |
| WO | WO 99/55696 A1 | 11/1999 |
| WO | WO 99/55896 | 11/1999 |
| WO | WO 99/64044 | 12/1999 |
| WO | WO 99/64044 A1 | 12/1999 |
| WO | WO 99/65894 | 12/1999 |
| WO | WO 00/26202 | 5/2000 |
| WO | WO 00/31063 | 6/2000 |
| WO | WO 00/26202 | 11/2000 |
| WO | WO 00/67802 | 11/2000 |
| WO | WO 00/71535 A1 | 11/2000 |
| WO | WO 01/12189 A1 | 2/2001 |
| WO | WO 01/17516 A2 | 3/2001 |
| WO | WO 01/19830 A1 | 3/2001 |
| WO | WO 01/22954 A2 | 4/2001 |
| WO | WO 01/47913 A2 | 7/2001 |
| WO | WO 01/47916 A1 | 7/2001 |
| WO | WO 01/94310 A1 | 12/2001 |
| WO | WO 02/08225 A1 | 1/2002 |

OTHER PUBLICATIONS

Chinese Search Rpt, Jun. 16, 2004.
Russion search rpt w/ translation, Apr. 2003.
Norwegian search rpt w/ translation, Mar. 2006.
Bacher Gerald et al, D-24851, A Novel Synthetic Microtubule Inhibitor, Exerts Curative Antitumoral Activity in Vivo, Shows efficacy toward multidrug-resistant tumor cells, and Lacks Nerotoxicity,; Cancer Research, American Associaton for Cancer Research. Baltimore, MD, US, Bd. 61, Nr. 1, 2001, Seiten 392-399, XP-002173885.

(Continued)

*Primary Examiner* — Peter G O'Sullivan
(74) *Attorney, Agent, or Firm* — Goodwin Procter LLP (57) ABSTRACT

The invention relates to novel indole derivatives of the general formula 1, to their preparation and to their use as medicaments, in particular for treating tumors.

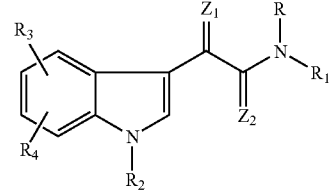

Formula 1

11 Claims, 1 Drawing Sheet

OTHER PUBLICATIONS

Database CA [Online] Chemical Abstracts Service, Columbus, Ohio, US; Fresneda, Pilar M. et al: Microwave-assisted regioselective synthesis of 2,4-disubstituted imidazoles: imidazoles: nortopsentin D synthesized by minimal effort; retrieved from STN, Database accession No. 134;281011, XP-002193292, 2001.

Bianucci, Anna Maria et al: "Benzodiazepine Receptor Affinity and Interaction of Some n-(indol-3-ylglyoxylyl) amine Derivatives"; J, Med. Chem. (1992), 35(12), 2214-20, XP-001056519.

Database CA [Online] Chemical Abstracts Service, Columbus, Ohio, US; Polymeropoulos, E. E. et al: "a Peptiedic Binding Site Model for PDE 4 Inhibitors"; retrieved from STN, Database accession No. 134:360953; XP-002193285, 2000.

Database CA [Online] Chemical Abstracts Service, Columbus, Ohio, US; Podwinski, Bohdan: "Synthesis of Some 5-benzyloxyindole-3-glyoxylic acid amides"; retrieved from STN, Database accession No. 70:37598; XP-002193286, 1966.

Polymeropoulos E. E. et al: "A Peptidic Binding Site Model for PDE 4 Inhitibors"; Quantitative Structure-Activity Relationships, VCH Publishers, Deerfield Beach, FL, US, Bd. 18, Nr. 6, 1999, Seitern 543-547, XP-001022210.

Battaglia, Sandra et al: "Indole Amide Derivatives: Synthesis, Structure-activity Relationships and Molecular Modeling Studies of A New Seires of Histamine H1-receptor Atagonists"; Eur. J. Med, Chem. (1999), 34(2), 93-105, XP-002193281.

Jiang, B. et al: "Synthesis and Cytotoxicity Evaluation of Bis(indlyl) thiazole, Bls(indolyl) pyrazinone and Bis(indolyl)pyrazine: analogues of Cytotoxic Marine Bis(indole) alkaloid"; Bioorg. Med, Chem. (2000), 8(2), 363-371, XP-002193282.

Faul, Margaret M. et al: "A New, Efficient Method for the Synthesis of Bisindolylmaleimides"; J. Org. Chem. (1998), 63(17), 6053-6058, XP-002193283.

Database CA [Online] Chemical Abstracts Service, Columbus, Ohio, US; Sarstedt, Burkhard et al: "Reactions with Indole Derivatives. XLVIII. A Simple Synthesis of the Staurosporine Aglycon" retrieved from STN, Database accession No. 98;215863; XP-002193287, 1983.

Database CA [Online] Chemical Abstracts Service, Columbus, Ohio, US; Povalyaeva, O.S. et al: "Synthesis and Properties of N-substituted 4-amino-1, 2-dithiolanes and Related Compounds"; retrieved from STN, Database accession No. 101-72646; XP-002193268, 1984.

Database CA [Online] Chemical Abstracts Service, Columbus, Ohio, US; Afsah, El Sayed M. et al: "Synthesis and Reactions of N-indol-3-ylmethylakylamines and Related Compounds"; retrieved form STN, Database accession No. 102:6101; XP-002193289, 1989.

Database CA [Online] Chemical Abstracts Service, Columbus, Ohio, US; Jiang, Biao et al: "Total Synthesis of (.+-.)-Dragmacidin; A Cytotoxic Bis(indole)alkaloid of Marine Origin"; retrieved from STN, Database accesssion No. 11:280941; XP-002193290, 1994.

Database CA [Online] Chemical Abstracts Service, Columbus, Ohio, US; Martini, Claudia et al; "Specific Inhibition of Benzodiazepine Receptor Binding by Some N-(Indol-3-ylglyoxylyl)amino acid Derivatives"; retrieved from STN, Database accession No. 102:125088, XP-002193291, 1985.

Evans S.M. et al: "Probing the 5-TH3 Receptor Site Using Novel Indole-3-Glyoxylic Acid Derivatives" Medicinal Chemistry Research, Birkhaeuser, Boston, US, Bd. 3, Nr. 5/6, 1993, Seiten 386-406, XP-000956190.

Database CA [Online] Chemical Abstracts Service, Columbus, Ohio, US; Da Settimo, A. et al: "Synthesis and anti-inflammatory Activity of Some N-(5-substituted indol-3-ylglyoxyl)amine Derivatives"; retrieved from STN, Database accession No. 107:32773. XP-002193264, 1987.

Organic Chemistry Journal, vol. 20, No. 4, 1984, pp. 849-860, compounds XVIb and XIIb, p. 859.

Heterocycles, (1983), 20(3), pp. 469-476, compounds 8 and 10, pp. 471 and 473-474.

J. Med Chem., (1992), 35, (12), pp. 2214-2220, compounds 2-6 from tables 1 and 2.

J. Chem. Soc. Perkin Trans. I 1984, pp. 1929-1932.

Chemical Abstracts, 70:37598; compound with registry Nos. 21421-40-9 and compound with registry No. 21421-41-0, 1966.

Chemical Abstracts, 134:360953; compound with registry Nos. 340719-96-2, 2000.

"Clonogenic assay with established human tumour xenografts: correlation of in vitro to in vivo activity as a basis for anticancer drug discovery" H.H. Fiebig et al. European Journal of Cancer 2004, 40, 802-820.

Search report from Belarus Patent Office, 2001.

\* cited by examiner

Figure 1.

Tab. 1 In vitro cytotoxicity of D-69429 in tumor cell lines (Curves determined for 8 substance concentrations)

| Growth inhibiton, IC50 [μM] | |
|---|---|
| KB/Hela | 0.17 |
| SKOV3 | 0.17 |
| MCF7 | 0.26 |
| L1210 | 0.35 |

INDOLE DERIVATIVES AND THEIR USE AS MEDICAMENT

CROSS-REFERENCE TO RELATED APPLICATIONS

This application is a continuation of U.S. application Ser. No. 12/004,168, filed on Dec. 20, 2007, which is a divisional of U.S. application Ser. No. 09/910,140, filed on Jul. 20, 2001 now U.S. Pat. No. 7,365,081. This application incorporates by reference the contents of co-pending application Ser. No. 12/004,169, filed on Dec. 20, 2007.

The invention relates to novel indole derivatives of the general formula 1, to their preparation and to their use as medicaments, in particular for treating tumors.

BACKGROUND

Indol-3-yl derivatives having certain 2-, 3-, 4- and 8-quinoline radicals are described in the German application DE 198 14 838.0. However, indol-3-yl derivatives having 5-, 6- or 7-quinoline substituents are neither described nor suggested in this publication.

SUMMARY

According to one aspect of the invention, novel indole derivatives of the general formula 1

Formula 1 in which
R denotes hydrogen; straight-chain or branched $(C_1-C_6)$-alkyl; $(C_1-C_6)$-alkyl which is mono- or polysubstituted by aryl, where the aryl radical [lacuna] unsubstituted or mono- to penta-[lacuna] by identical or different substituents from the group consisting of halogen, $(C_1-C_6)$-alkyl, $(C_3-C_7)$-cycloalkyl, carboxyl, $(C_1-C_8)$-alkoxycarbonyl, preferably tert-butoxycarbonyl, straight-chain or branched $(C_1-C_6)$-alkyl, which is substituted by one or more fluorine atoms, preferably trifluoromethyl, hydroxyl, straight-chain or branched $(C_1-C_6)$-alkoxy, preferably methoxy or ethoxy; benzyloxy or aryl-$(C_1-C_6)$-alkyl, where the aryl radical may be unsubstituted or mono- or pentasubstituted by identical or different substituents from the group consisting of $(C_1-C_6)$-alkyl, halogen and straight-chain or branched $(C_1-C_6)$-alkyl which is substituted by one or more fluorine. atoms, preferably. trifluoromethyl; straight-chain or branched $(C_1-C_6)$-alkoy-$(C_1-C_6)$-alkyl [sic], substituted or unsubstituted aryl-$(C_1-C_6)$-alkyloxycarbonyl, preferably benzyloxycarbonyl, straight-chain or branched $(C_1-C_6)$-alkyloxycarbonyl, straight-chain or branched $(C_1-C_6)$-alkylcarbonyl, preferably acetyl, $(C_2-C_6)$-alkenyl, preferably allyl, $(C_2-C_6)$-alkynyl, preferably ethynyl or propargyl, or straight-chain or branched cyano-$(C_1-C_6)$-alkyl, preferably cyanomethyl;

$R_1$ denotes a saturated, unsaturated or aromatic (C2-C14)-heterocycle which contains one or more heteroatoms selected from the group consisting of N, O and S and which may be attached to the amide nitrogen directly or via a (C1-C6)-alkyl bridge, where the $(C_1-C_4)$-alkyl radical may be unsubstituted or mono- [lacuna] polysubstituted by identical or different substituents from the group consisting of $(C_1-C_6)$-alkyl, halogen and oxo (=O) and the 2-, 4-, 5- or 6-pyrimidinyl radical may in each case be unsubstituted or mono- to trisubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl, with the proviso that R1 does not represent unsubstituted 2- or 4-pyrimidinyl or a 2-pyrimidinyl radical which is mono- or polysubstituted by methyl; and except for (C1-C6)-alkyl-, halogen-, nitro-, amino- and (C1-C6)-alkylamino-substituted or unsubstituted 2-, 3-, 4- and 8-quinolyl and 2-, 3- and 4-quinolylmethyl in which the ring carbon atoms of the pyridylmethyl moiety are unsubstituted or substituted by (C1-C6)-alkyl, (C1-C6)-alkoxy, nitro, amino and (C1-C6)-alkoxycarbonylamino;

$R_2$ denotes hydrogen, $(C_1-C_6)$-alkyl, $(C_1-C_6)$-alkyl which is mono- or polysubstituted by halogen, $(C_1-C_6)$-alkyl which is mono- or polysubstituted by phenyl, where the phenyl radical may be unsubstituted or mono- to pentasubstituted by identical or different substituents from the group consisting of halogen, preferably chlorine, bromine or iodine, $(C_1-C_6)$-alkyl, $(C_3-C_7)$-cycloalkyl, carboxyl, $(C_1-C_6)$-alkoxycarbonyl, $(C_1-C_6)$-alkyl which is mono- or polysubstituted by halogen, preferably trifluoromethyl, hydroxyl, $(C_1-C_6)$-alkoxy, preferably methoxy or ethoxy, phenyl-$(C_1-C_6)$-alkoxy, preferably benzyloxy, nitro, amino, mono-$(C_1-C_6)$-alkylamino, di-$(C_1-C_6)$-alkylamino, mono-$(C_{3-6})$-cycloalkylamino, di-$(C_{3-6})$-cycloalkylamino, $(C_1-C_6)$-acylamino, phenyl-$(C_1-C_6)$-alkylamino, arylcarbonylamino, heteroarylcarbonylamino, $(C_1-C_6)$-alkylsulfonamido, arylsulfonamido, maleinimido, succinimido, phthalimido, benzyloxycarbonylamino (Z-amino), tert-butoxycarbonylamino (BOC-amino), 9-fluorenylmethoxycarbonylamino (Fmoc-amino), triphenylmethylamino (Tr-amino), 2-(4'-pyridyl)-ethoxycarbonylamino (Pyoc-amino), diphenylmethylsilylamino (DPMS-amino), by —NH—$CH_2$—COOH, —NH—CH$(CH_3)$—COOH; $(CH_3)_2$CH—$CH_2$—$CH_2$—CH(NH—)—COOH; $H_3$C—$CH_2$—CH$(CH_3)$—CH(NH—)—COOH; HO$H_2$C—CH(NH—)—COOH; phenyl-$CH_2$—CH(NH—)—COOH; (4-imidazolyl)-$CH_2$—CH(NH—)—COOH; HN=C($NH_2$)—NH—$(CH_2)_3$—CH(NH—)—COOH; $H_2$N—$(CH_2)_4$—CH(NH—)—COOH; $H_2$N—CO—$CH_2$—CH(NH—)—COOH; HOOC—$(CH_2)_2$—CH(NH—)—COOH;

a 2-, 3-, 4-, 5-, 6-, 7- and 8-quinolyl-$(C_1-C_6)$-alkyl radical, where the 2-, 3-, 4-, 5, -, [sic] 6-, 7- and 8-quinolyl radical may be unsubstituted or mono- to hexasubstituted by identical or different substituents from the group consisting of halogen, $(C_1-C_4)$-alkyl or $(C_1-C_4)$-alkoxy;

a 2-, 3- and 4-pyridyl-$(C_1-C_6)$-alkyl radical, where the 2-, 3- and 4-pyridyl radical may be unsubstituted or mono- to tetrasubstituted by identical or different substituents from the group consisting of halogen, $(C_1-C_4)$-alkyl and $(C_1-C_4)$-alkoxy;

an arylcarbonyl radical, where the aryl radical may be unsubstituted or mono- to pentasubstituted by identical or different substituents from the group consisting of halogen, $(C_1-C_6)$-alkyl, $(C_3-C_7)$-cycloalkyl, carboxyl, cyano, $(C_1-C_6)$-alkoxycarbonyl, $(C_1-C_6)$-alkyl which is mono- or polysubstituted by fluorine atoms preferably trifluoromethyl, hydroxyl, $(C_1-C_4)$-alkoxy preferably methoxy or ethoxy, aryl-$(C_1-C_4)$-alkoxy, preferably benzyloxy;

$R_3$ and $R_4$ may be attached to the indole carbon atoms C-2, C4, C-5, C6 or C-7 and independently of one another denote hydrogen, hydroxyl, $(C_1-C_6)$-alkyl, $(C_3-C_7)$-cycloalkyl, $(C_1-C_6)$-alkylcarbonyl, $(C_1-C_6)$-alkoxy, halogen, aryl-$(C_1-C_4)$-alkoxy, preferably benzyloxy, nitro, amino, mono-$(C_1-C_4)$-alkylamino, di-$(C_1-C_4)$-alkylamino, $(C_1-C_6)$-alkoxycarbonylamino, $(C_1-C_6)$-alkoxycarbonylamino-$(C_1-C_6)$-alkyl, cyano, straight-chain or branched cyano-$(C_1-C_6)$-alkyl, carboxyl, $(C_1-C_4)$-alkoxycarbonyl, $(C_1-C_4)$-alkyl which is substituted by one or more fluorine atoms, preferably trifluoromethyl group, carboxy-$(C_1-C_6)$-alkyl or $(C_1-C_6)$-alkoxycarbonyl-$(C_1-C_6)$-alkyl;

$Z_1$ denotes oxygen or sulfur or geminally attached hydrogen and hydroxyl;

$Z_2$ denotes oxygen or sulfur, their tautomers, stereoisomers, including the diastereomers and enantiomers, and the physiologically acceptable salts thereof, are provided.

DETAILED DESCRIPTION OF THE EMBODIMENTS

Thus, for example, the compounds of the general formula (1) according to the invention which have one. or more centers of chirality and which are present as racemates can be separated by methods known per se into their optical isomers, i.e. enantiomers or diastereomers. The separation can be carried out by column separation on chiral phases or by recrystallization from an optically active solvent or using an optically active acid or base or by derivatization with an optically active reagent, such as, for example, an optically active alcohol, and subsequent removal of the radical.

Furthermore, the indole derivatives of the formula (1) according to the invention can be converted into their salts with inorganic or organic acids, in particular, for pharmaceutical use, into their physiologically acceptable salts. Acids which are suitable for this purpose are, for example, hydrochloric acid, hydrobromic acid, sulfuric acid, phosphoric acid, fumaric acid, succinic acid, lactic acid, malic acid, embonic acid, malonic acid, citric acid, acetic acid, tartaric acid, trifluoroacetic acid, methanesulfonic acid, sulfoacetic acid or maleic acid.

Moreover, the compounds of the formula (1) according to the invention can, if they contain a sufficiently acidic group, such as a carboxyl group, be converted, if desired, into their salts with inorganic or organic bases, in particular, for pharmaceutical use, into their physiologically acceptable salts. Bases which are suitable for this purpose are, for example, sodium hydroxide, potassium hydroxide, calcium hydroxide, lysine, cyclohexylamine, ethanolamine, diethanolamine and triethanolamine.

According to a preferred embodiment, indole derivatives of the general formula (1) above are provided in which R, R2, R3, R4, Z1 and Z2 have the meanings given above and $R_1$ denotes a 2-, 4-, 5- or 6-pyrimidinyl radical or 2-, 4-, 5- or 6-pyrimidinyl-$(C_1-C_4)$-alkyl radical, where the $(C_1-C_4)$-alkyl radical may be unsubstituted or mono-[lacuna] polysubstituted by identical or different substituents from the group consisting of $(C_1-C_6)$-alkyl, halogen and oxo (=O) and the 2-, 4-, 5- or 6-pyrimidinyl radical may be unsubstituted or mono- to trisubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl, or $(C_6-C_{10})$-aryl-$(C_1-C_6)$-alkyl, with the proviso that R1 does not represent unsubstituted 2- or 4-pyrimidinyl or a 2-pyrimidinyl radical which is mono- or polysubstituted by methyl;

a 3-, 4-, 5- or 6-pyridazinyl radical or 3-, 4-, 5- or 6-pyridazinyl-$(C_1-C_4)$-alkyl radical, where the $(C_1-C_4)$-alkyl radical may be unsubstituted or mono- or polysubstituted by identical or different substituents from the group consisting of $(C_1-C_6)$-alkyl, halogen and oxo (=O) and the 3-, 4-, 5- or 6-pyridazinyl radical may be unsubstituted or mono- to trisubstituted by. identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 3-, 5- or 6-pyrazinyl radical or 2-, 3-, 5, -[sic] or 6-pyrazinyl-$(C_1-C_4)$-alkyl radical, where the $(C_1-C_4)$-alkyl radical may be unsubstituted or mono- or polysubstituted by identical or different substituents from the group consisting of $(C_1-C_6)$-alkyl, halogen and oxo (=O) and the 2-, 3-, 5, -[sic] or 6-pyrazinyl radical may be unsubstituted or mono- to trisubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 3-, 4-, 5-, 6-, 7- or 8-cinnolinyl radical or 3-, 4-, 5-, 6-, 7-, or 8-cinnolinyl-$(C_1-C_4)$-alkyl radical, where the $(C_1-C_4)$-alkyl radical may be unsubstituted or mono- or polysubstituted by identical or different substituents from the group consisting of $(C_1-C_6)$-alkyl, halogen and oxo (=O) and the 3-, 4-, 5-, 6-, 7-, or 8-cinnolinyl radical may be unsubstituted or mono- to pentasubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 4-, 5-, 6-, 7- or 8quinazolinyl radical or 2-, 4-, 5-, 6-, 7- or 8-quinazolinyl-$(C_1-C_4)$-alkyl radical, where the $(C_1-C_4)$-alkyl radical may be unsubstituted or mono- or polysubstituted by identical or different substituents from the group consisting of hydrogen, $(C_1-C_6)$-alkyl, halogen and oxo (=O) and the or [sic] 2-, 4-, 5-, 6-, 7- or 8-quinazolinyl radical may be unsubstituted or mono- to pentasubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 3-, 5-, 6-, 7- or 8-quinoxalinyl radical or 2-, 3-, 5-, 6-, 7- or 8-quinoxalinyl-$(C_1-C_4)$-alkyl radical, where the $(C_1-C_4)$-alkyl radical may be unsubstituted or mono- or polysubstituted by identical or different substituents from the group consisting of $(C_1-C_6)$-alkyl, halogen and oxo (=O) and the or [sic] 2-, 3-, 5-, 6-, 7- or 8-quinoxalinyl radical may be unsubstituted or mono- to pentasubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 4-, 5-, 6-, 7- or 8-phthalazinyl radical or 1-, 4-, 5-, 6-, 7- or 8-phthalazinyl-$(C_1-C_4)$-alkyl radical, where the $(C_1-C_4)$-alkyl radical may be unsubstituted or mono- or polysubstituted by identical or different substituents from the group consisting of $(C_1-C_6)$-alkyl, halogen and oxo (=O) and the or [sic] 1-, 4-, 5-, 6-, 7- or 8-phthalazinyl radical may be unsubstituted or mono- to pentasubstituted. by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 3-, 4-, 5-, 6-, 7- or 8-quinolyl radical or 2-, 3-, 4-, 5-, 6-, 7 or 8-quinolyl-$(C_1-C_4)$-alkyl radical, where the $(C_1-C_4)$-alkyl radical may be unsubstituted or mono- or polysubstituted by identical or different substituents from the group consisting of $(C_1-C_6)$-alkyl, halogen and oxo (=O) and the 2-, 3-, 4-, 5-, 6-, 7- or 8-quinolyl radical may be unsubstituted or mono- to hexasubstituted by identical or different substituents from the group consisting of hydrogen, $(C_1-C_6)$-alkyl, preferably methyl, particularly preferably 2-methyl, halogen, nitro, amino, mono-$(C_1-C_6)$-alkylamino, N,N-di-$(C_1-C_6)$-alkylamino, hydroxyl, $(C_1-C_6)$-alkoxy, (C6-C14)-aryl-(C1-C6)-alkyoxy [sic], preferably benzyloxy, carboxyl, $(C_1-C_6)$-alkoxycarbonyl, $(C_1-C_6)$-alkoxycarbonylamino or $(C_1-C_6)$-alkyl which is mono- or polysubstituted by halogen, preferably trifluoromethyl, $(C_6-C_{14})$-aryl and $(C_6-C_{14})$-aryl-$(C_1-C_6)$-alkyl, except for (C1-C6)-alkyl-, halogen-, nitro-, amino- and (C1-C6)-alkylamino-substituted or unsubstituted 2-, 3-, 4- and 8-quinolyl and 2-, 3- and 4-quinolylmethyl in which the ring carbon atoms of the pyridylmethyl moiety are unsubstituted or substituted by (C1-C6)-alkyl, (C1-C6)-alkoxy, nitro, amino and (C1-C6)-alkoxycarbonylamino;

a 1-, 3-, 4-, 5-, 6-, 7- or 8-isoquinolyl radical or 1-, 3-, 4-, 5-, 6-, 7- or 8-isoquinolyl-$(C_1-C_4)$-alkyl radical, where the $(C_1-C_4)$-alkyl radical may be unsubstituted or mono- or polysubstituted by identical or different substituents from the group consisting of $(C_1-C_6)$-alkyl, halogen and oxo (=O) and the 1-, 3-, 4-, 5-, 6-, 7- or 8-isoquinolyl radical may be unsubstituted or mono- to hexasubstituted by identical or different substituents from the group consisting of hydrogen, $(C_1-C_6)$-alkyl, halogen, nitro, amino, mono-$(C_1-C_8)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 6-, 8- or 9-[9H]-purinyl radical or 2-, 6-, 8- or 9-[9H]-purinyl-$(C_1-C_4)$-alkyl radical, where the $(C_1-C_4)$-alkyl radical may be unsubstituted or mono- or polysubstituted by identical or different substituents from the group consisting of $(C_1-C_6)$-alkyl, halogen and oxo (=O) and the 2-, 6-, 8- or 9-[9H]-purinyl radical may be unsubstituted or mono- to trisubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 6-, 7- or 8-[7H]-purinyl radical or 2-, 6-, 7- or 8-[7H]-purinyl-$(C_1-C_4)$-alkyl radical, where the $(C_1-C_4)$-alkyl radical may be unsubstituted or mono- or polysubstituted by identical or different substituents from the group consisting of $(C_1-C_6)$-alkyl, halogen and oxo (=O) and the 2-, 6-, 7- or 8-[7]-purinyl radical may be unsubstituted or mono- to trisubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 2-, 3-, 4-, 5-, 6-, 7-, 8- or 9-acridinyl radical or 1-, 2-, 3-, 4-, 5-, 6-, 7-, 8- or 9-acridinyl-$(C_1-C_4)$-alkyl radical, where the $(C_1-C6)$-alkyl radical may be unsubstituted or mono- or polysubstituted by identical or different substituents from the group consisting of $(C_1-C_6)$-alkyl, halogen and oxo (=O) and the 1-, 2-, 3-, 4-, 5-, 6-, 7-, 8- or 9-acridinyl radical may be unsubstituted or mono- to octasubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 2-, 3-, 4-, 6-, 7-, 8-, 9- or 10-phenanthridinyl radical or 1-, 2-, 3-, 4-, 6-, 7-, 8- or 9- or 10-phenanthridinyl-$(C_1-C_6)$-alkyl radical, where the $(C_1-C_6)$-alkyl radical may be unsubstituted or mono- or polysubstituted by identical or different substituents from the group consisting of hydrogen, $(C_1-C_6)$-alkyl, halogen and oxo (=O) and the 1-, 2-, 3-, 4-, 6-, 7-, 8-, 9- or 10-phenanthridinyl radical may be unsubstituted or mono- to octasubstituted by identical or different substituents from the group consisting of $(C_1-C_6)$-alkyl, halogen, nitro, amino, mono- ($C_1$-$C_6$)-alkylamino, di-($C_1$-$C_6$)-alkylamino, hydroxyl, ($C_1$-$C_6$)-alkoxy, ($C_6$-$C_{10}$)-aryl-($C_1$-$C_6$)-alkoxy, preferably benzyloxy, carboxyl, ($C_1$-$C_6$)-alkoxycarbonyl, ($C_1$-$C_6$)-alkoxycarbonylamino or ($C_1$-$C_6$)-alkyl which is mono- or polysubstituted by fluorine, preferably trifluoromethyl, ($C_6$-$C_{10}$)-aryl and ($C_6$-$C_{10}$)-aryl-($C_1$-$C_6$)-alkyl;

a 2-, 3-, 4-, 5, -[sic] or 6-pyridyl radical where the 2-, 3-, 4-, 5, -[sic] or 6-pyridyl radical may be unsubstituted or mono- to tetrasubstituted by identical or different substituents from the group consisting of hydrogen, ($C_1$-$C_6$)-alkyl, halogen, nitro, amino, mono-($C_1$-$C_6$)-alkylamino, di-($C_1$-$C_6$)-alkylamino, hydroxyl, ($C_1$-$C_6$)-alkoxy, benzyloxy, carboxyl, ($C_1$-$C_6$)-alkoxycarbonyl, ($C_1$-$C_6$)-alkoxycarbonylamino or ($C_1$-$C_6$)-alkyl which is mono- or polysubstituted by fluorine, preferably trifluoromethyl, ($C_6$-$C_{10}$)-aryl and ($C_6$-$C_{10}$)-aryl-($C_1$-$C_6$)-alkyl, with the proviso that $Z_1$, $Z_2$, $R_2$, $R_3$ and $R_4$ have the meaning given above or below, without any limitations, and R represents ($C_2$-$C_6$)-alkenyl, preferably allyl, ($C_2$-$C_6$)-alkynyl, preferably ethynyl or propargyl, ($C_1$-$C_6$)-alkoxy-($C_1$-$C_6$)-alkyl, or straight-chain or branched cyano-$C_1$-$C_6$-alkyl, preferably cyanomethyl, or with the proviso that $Z_2$, R, $R_2$, $R_3$ and $R_4$ have the meanings described above or below, without any limitations, and $Z_1$ denotes geminally attached hydrogen and hydroxyl;

a 2-, 3-, 4-, 5, -[sic] or 6-pyridyl-($C_1$-$C_6$)-alkyl radical, where the ($C_1$-$C_6$)-alkyl radical may be unsubstituted or mono- or polysubstituted by identical or different substituents from the group consisting of ($C_1$-$C_6$)-alkyl, halogen and oxo (=O) and the 2-, 3-, 4-, 5, -[sic] or 6-pyridyl radical may be unsubstituted or mono- to tetrasubstituted by identical or different substituents from the group consisting of hydrogen, ($C_1$-$C_6$)-alkyl, halogen, nitro, amino, mono-($C_1$-$C_6$)-alkylamino, di-($C_1$-$C_6$)-alkylamino, hydroxyl, ($C_1$-$C_6$)-alkoxy, benzyloxy, carboxyl, ($C_1$-$C_6$)-alkoxycarbonyl, ($C_1$-$C_6$)-alkoxycarbonylamino or ($C_1$-$C_6$)-alkyl which is mono- or polysubstituted by fluorine, preferably trifluoromethyl, ($C_6$-$C_{10}$)-aryl and ($C_6$-$C_{10}$)-aryl-($C_1$-$C_6$)-alkyl;

a 2-, 3-, 4, -[sic] or 5-thienyl radical or 2-, 3-, 4, -[sic] or 5-thienyl-($C_1$-$C_6$)-alkyl radical, where the ($C_1$-$C_6$)-alkyl radical may be unsubstituted or mono- or polysubstituted by identical or different substituents from the group consisting of ($C_1$-$C_6$)-alkyl, halogen and oxo (=O) and the 2-, 3-, 4, -[sic] or 5-thienyl radical may be unsubstituted or mono- to trisubstituted by identical or different substituents from the group consisting of hydrogen, ($C_1$-$C_6$)-alkyl, halogen, nitro, amino, mono-($C_1$-$C_6$)-alkylamino, di-($C_1$-$C_6$)-alkylamino, hydroxyl, ($C_1$-$C_6$)-alkoxy, benzyloxy, carboxyl, ($C_1$-$C_6$)-alkoxycarbonyl, ($C_1$-$C_6$)-alkoxycarbonylamino or ($C_1$-$C_6$)-alkyl which is mono- or polysubstituted by fluorine, preferably trifluoromethyl, ($C_6$-$C_{10}$)-aryl and ($C_6$-$C_{16}$)-aryl-($C_1$-$C_6$)-alkyl;

a 2-, 4-, or 5-thiazolyl radical or 2-, 4-, or 5-thiazolyl-($C_1$-$C_6$)-alkyl radical, where the ($C_1$-$C_6$)-alkyl radical may be unsubstituted or mono- or polysubstituted by identical or different substituents from the group consisting of ($C_1$-$C_6$)-alkyl, halogen and oxo (=O) and the 2-, 4-, or 5-thiazolyl radical may be unsubstituted or mono- or disubstituted by identical or different substituents from the group consisting of hydrogen, ($C_1$-$C_6$)-alkyl, halogen, nitro, amino, mono-($C_1$-$C_6$)-alkylamino, di-($C_1$-$C_6$)-alkylamino, hydroxyl, ($C_1$-$C_6$)-alkoxy, benzyloxy, carboxyl, ($C_1$-$C_6$)-alkoxycarbonyl, ($C_1$-$C_6$)-alkoxycarbonylamino or ($C_1$-$C_6$)-alkyl which is mono- or polysubstituted by fluorine, preferably trifluoromethyl, ($C_6$-$C_{10}$)-aryl and ($C_6$-$C_{10}$)-aryl-$C_1$-$C_6$)-alkyl;

a 3-, 4-, or 5-isothiazolyl radical or 3-, 4- or 5-isothiazolyl-($C_1$-$C_6$)-alkyl radical, where the ($C_1$-$C_6$)-alkyl radical may be unsubstituted or mono- or polysubstituted by identical or different substituents from the group consisting of ($C_1$-$C_6$)-alkyl, halogen and oxo (=O) and the 3-, 4- or 5-isothiazolyl radical may be unsubstituted or mono- or disubstituted by identical or different substituents from the group consisting of hydrogen, ($C_1$-$C_6$)-alkyl, halogen, nitro, amino, mono-($C_1$-$C_6$)-alkylamino, di-($C_1$-$C_6$)-alkylamino, hydroxyl, ($C_1$-$C_6$)-alkoxy, benzyloxy, carboxyl, ($C_1$-$C_6$)-alkoxycarbonyl, ($C_1$-$C_6$)-alkoxycarbonylamino or ($C_1$-$C_6$)-alkyl which is mono- or polysubstituted by fluorine, preferably trifluoromethyl, ($C_6$-$C_{10}$)-aryl and ($C_6$-$C_{10}$)-aryl-$C_1$-$C_6$)-alkyl;

a 2-, 4-, 5-, 6- or 7-benzothiazolyl radical or 2-, 4-, 5-, 6- or 7-benzothiazolyl-($C_1$-$C_6$)-alkyl radical, where the ($C_1$-$C_6$)-alkyl radical may be unsubstituted or mono- or polysubstituted by identical or different substituents from the group consisting of ($C_1$-$C_6$)-alkyl, halogen and oxo (=O) and the 2-, 4-, 5-, 6- or 7-benzothiazolyl radical may be unsubstituted or mono- to tetrasubstituted by identical or different substituents from the group consisting of hydrogen, ($C_1$-$C_6$)-alkyl, halogen, nitro, amino, mono-($C_1$-$C_6$)-alkylamino, di-($C_1$-$C_6$)-alkylamino, hydroxyl, ($C_1$-$C_6$)-alkoxy, benzyloxy, carboxyl, ($C_1$-$C_6$)-alkoxycarbonyl, ($C_1$-$C_6$)-alkoxycarbonylamino or ($C_1$-$C_6$)-alkyl which is mono- or polysubstituted by fluorine, preferably trifluoromethyl, ($C_6$-$C_{10}$)-aryl and ($C_6$-$C_{10}$)-aryl-($C_1$-$C_6$)-alkyl;

a 1-, 2-, 4- or 5-imidazolyl radical or 1-, 2-, 4- or 5-imidazolyl-($C_1$-$C_6$)-alkyl radical, where the ($C_1$-$C_6$)-alkyl radical may be unsubstituted or mono- or polysubstituted by identical or different substituents from the group consisting of ($C_1$-$C_6$)-alkyl, halogen and oxo (=O) and the 1-, 2-, 4- or 5-imidazolyl radical may be unsubstituted or mono- to trisubstituted by identical or different substituents from the group consisting of hydrogen, ($C_1$-$C_6$)-alkyl, halogen, nitro, amino, mono-($C_1$-$C_6$)-alkylamino, di-($C_1$-$C_6$)-alkylamino, hydroxyl, ($C_1$-$C_6$)-alkoxy, benzyloxy, carboxyl, ($C_1$-$C_6$)-alkoxycarbonyl, ($C_1$-$C_6$)-alkoxycarbonylamino or ($C_1$-$C_6$)-alkyl which is mono- or polysubstituted by fluorine, preferably trifluoromethyl, ($C_6$-$C_{10}$)-aryl and ($C_6$-$C_{10}$)-aryl-($C_1$-$C_6$)-alkyl;

a 1-, 3-, 4- or 5-pyrazolyl radical or 1-, 3-, 4- or 5-pyrazolyl-($C_1$-$C_6$)-alkyl radical, where the ($C_1$-$C_6$)-alkyl radical may be unsubstituted or mono- or polysubstituted by identical or different substituents from the group consisting of ($C_1$-$C_6$)-alkyl, halogen and oxo (=O) and the 1-, 3-, 4- or 5-pyrazolyl radical may be unsubstituted or mono- to trisubstituted by identical or different substituents from the group consisting of hydrogen, ($C_1$-$C_6$)-alkyl, halogen, nitro, amino, mono-($C_1$-$C_6$)-alkylamino, di-($C_1$-$C_6$)-alkylamino, hydroxyl, ($C_1$-$C_6$)-alkoxy, benzyloxy, carboxyl, ($C_1$-$C_6$)-alkoxycarbonyl, ($C_1$-$C_6$)-alkoxycarbonylamino or ($C_1$-$C_6$)-alkyl which is mono- or polysubstituted by fluorine, preferably trifluoromethyl, ($C_6$-$C_{10}$)-aryl and ($C_6$-$C_{10}$)-aryl-($C_1$-$C_6$)-alkyl;

a 1-, 2, -[sic] 3,-[sic] 4, -[sic] or 5-pyrrolyl radical or 1-, 2, -[sic] 3, -[sic] 4, -[sic] or 5-pyrrolyl-($C_1$-$C_6$)-alkyl radical, where the ($C_1$-$C_6$)-alkyl radical may be unsubstituted or mono- or polysubstituted by identical or different substituents from the group consisting of ($C_1$-$C_6$)-alkyl, halogen and oxo (=O) and the 1-, 2, -[sic] 3, -[sic] 4, -[sic] or 5-pyrrolyl radical may be unsubstituted or mono- to tetrasubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 3-, or 5-[1.2.4]-triazolyl radical or 1-, 3- or 5-[1.2.4]-triazolyl-$(C_1-C_6)$-alkyl radical, where the $(C_1-C_6)$-alkyl radical may be unsubstituted or mono- or polysubstituted by identical or different substituents from the group consisting of hydrogen, $(C_1-C_6)$-alkyl, halogen and oxo (=O) and the 1-, 3- or 5-[1.2.4]-triazolyl radical may be unsubstituted or mono- or disubstituted by identical or different substituents from the group consisting of $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 4- or 5-[1.2.3]-triazolyl radical or 1-, 4- or 5-[1.2.3]-triazolyl-$(C_1-C_6)$-alkyl radical, where the $(C_1-C_6)$-alkyl radical may be unsubstituted or mono- or polysubstituted by identical or different substituents from the group consisting of $(C_1-C_6)$-alkyl, halogen and oxo (=O) and the 1-, 4- or 5-[1.2.3]-triazolyl radical may be unsubstituted or mono- or disubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1- or 5-[1H]-tetrazolyl radical or 1- or 5-[1H]-tetrazolyl-$(C_1-C_6)$-alkyl radical, where the $(C_1-C_6)$-alkyl radical may be unsubstituted or mono- or polysubstituted by identical or different substituents from the group consisting of $(C_1-C_6)$-alkyl, halogen and oxo (=O) and the 1- or 5-[1H]-tetrazolyl radical may be unsubstituted or substituted by hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_8-C_{10})$-aryl and $(C_6-C_{10})$-aryl-$(C_1-C_6)$-alkyl;

a 2- or 5-[2H]-tetrazolyl radical or 2- or 5-[2H]-tetrazolyl-$(C_1-C_6)$-alkyl radical, where the $(C_1-C_6)$-alkyl radical may be unsubstituted or mono- or polysubstituted by identical or different substituents from the group consisting of $(C_1-C_6)$-alkyl, halogen and oxo (=O) and the 2- or 5-[2H]-tetrazolyl radical may be unsubstituted or substituted by hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 2-, 4- or 6-[1.3.5]-triazinyl radical or 2-, 4- or 6-[1.3.5]-triazinyl-$(C_1-C_6)$-alkyl radical, where the $(C_1-C_6)$-alkyl radical may be unsubstituted or mono- or polysubstituted by identical or different substituents from the group consisting of hydrogen,$(C_1-C_6)$-alkyl, halogen and oxo (=O) and the 2-, 4- or 6-[1.3.5]-triazinyl radical may be unsubstituted or mono- or disubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_1-C_{10})$-aryl and $(C_6-C_{10})$-aryl-$(C_1-C_6)$-alkyl;

a 2-, 4- or 5-oxazolyl radical or 2-, 4- or 5-oxazolyl-$(C_1-C_6)$-alkyl radical, where the $(C_1-C_6)$-alkyl radical may be unsubstituted or mono- or polysubstituted by identical or different substituents from the group consisting of $(C_1-C_6)$-alkyl, halogen and oxo (=O) and the 2-, 4-, or 5-oxazolyl radical may be unsubstituted or mono- or disubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 3-, 4- or 5-isoxazolyl radical or 3-, 4- or 5-isoxazolyl-$(C_1-C_6)$-alkyl radical, where the $(C_1-C_6)$-alkyl radical may be unsubstituted or mono- or polysubstituted by identical or different substituents from the group consisting of $(C_1-C_6)$-alkyl, halogen and oxo (=O) and the 3-, 4- or 5-isoxazolyl radical may be unsubstituted or mono- or disubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl;

a 1-, 2-, 3-, 4-, 5-, 6- or 7-indolyl radical or 1-, 2-, 3-, 4-, 5-, 6- or 7-indolyl-$(C_1-C_6)$-alkyl radical, where the $(C_1-C_6)$-alkyl radical may be unsubstituted or mono- or polysubstituted by identical or different substituents from the group consisting of $(C_1-C_6)$-alkyl, halogen and oxo (=O) and the 1-, 2-, 3-, 4-, 5-, 6- or 7-indolyl radical may be unsubstituted or mono- to hexasubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, preferably trifluoromethyl, $(C_6-C_{10})$-aryl and $(C_6-C_{10})$-aryl-$(C_1-C_6)$-alkyl, and also the isomers, in particular tautomers, diastereomers and enantiomers, and the pharmaceutically acceptable salts, in particular acid addition salts, thereof [lacuna].

According to a further embodiment, indole derivatives of the general formula (1) are provided which are characterized in that R, R2, R3, R4, Z1 and Z2 have the meanings described above and $R_1$ represents quinolyl which is mono- or a polysubstituted by straight-chain or branched $(C_1-C_6$-alkyl) or $(C_1-C_6)$-alkoxy.

According to a further embodiment, indole derivatives of the general formula (1) are provided which are characterized in that R, R2, R3, R4, Z1 and Z2 have the meanings described above and $R_1$ represents 2-methyl-6-quinolyl.

According to a further embodiment, indole derivatives of the general formula (1) are provided which are characterized in that R, R2, R3, R4, Z1 and Z2 have the meanings described above and $R_1$ denotes (2-methyl)-6-quinolyl, $R_2$ denotes 4-chlorobenzyl, $R_3$ and $R_4$ each denote hydrogen and $Z_1$ and $Z_2$ each denote oxygen.

According to a further aspect of the invention, a process for preparing indole derivatives of the general formula (1) according to any of claims 1 to 5 is [lacuna] which is characterized in that an indole precursor of the general formula (2)

Formula 2 in which R2, R3 and R4 have the meanings mentioned above is reacted with a compound of the general formula (3)

Formula 3 in which Z1 and Z2 have the meaning mentioned above and Y1 and Y2 independently of one another represent a suitable leaving group, such as halogen, (C1-C6)-alkoxy, —O-tosyl, —O-mesyl or —N1-imidazole, and then with an amine of the general formula (4) or (5)

Formula 4

Formula 5 in which R and R1 have the meanings mentioned above, giving the desired indole derivative of the general formula (1) (with amine 4) or the compound of the general formula (6) (with amine 5)

Formula 6 in which R1, R2, R3, R4, Z1 and Z2 have the meanings mentioned above, using, if appropriate, diluents and auxiliaries, where the compound of the general formula (6) may subsequently be reacted with a compound of the general formula (7)

R—Y3     (7)

in which R has the meaning mentioned above and $Y_3$ represents a suitable electrophilic leaving group, such as halogen, (C1-C6)-alkoxy, —O-tosyl, —O-mesyl or —N1-imidazole, giving the desired compound (1), where R does not denote hydrogen, using, if appropriate, diluents and auxiliaries.

Synthesis Routes:

The compounds of the general formula 1 can be obtained according to Scheme 1 below:

Furthermore, the compounds of the general formula 1 can also be obtained by the synthesis route of Scheme 2:

-continued

2. Step

The compounds of the general formula 1 in which R=methyl, benzyl, propargyl or cyanomethyl and $R_1$, $R_2$, $R_3$ and $R_4$ have the meanings given for the general formula 1 can also be prepared according to the synthesis route of Scheme 3:

Scheme 3

The starting materials (2), (3) and (4) are either commercially available or can be prepared by procedures known per se. The starting materials (2), (3) and (4) are useful intermediates for preparing the indole derivatives of the formula (1) according to the invention.

For the preparation of starting materials and target compounds, reference may be made, for example, to the following standard works of organic synthesis, the content of which is hereby explicitly included into the disclosure of the present application:

1) Houben-Weyl, Volume E 7a (part 1) pp. 290-492, pp. 571-740 Houben-Weyl, Volume E 7a (part 2) pp. 119-156, pp. 205-686, pp. 157-204

2) Monograph "Heterocyclic Compounds" (Elderfield), Volume 1, pp. 119-207, pp. 397-616
Volume 3, pp. 1-274
Volume 6, pp. 101-135, pp. 234-323

3) Monograph "Comprehensive Organic Chemistry" (S. D. Barton, W. D. Ollis)
Volume 4, pp. 155-204, pp. 205-232, pp. 493-564

The solvents and auxiliaries to be used, if appropriate, and the reaction parameters to be used, such as reaction temperature and reaction time, are known to the person skilled in the art owing to his expert knowledge.

The indole derivatives of the general formula (1) according to the invention are suitable as medicaments, in particular as antitumor agents, for treating mammals, in particular man, but also domestic animals such as horses, cattle, dogs, cats, hares, sheep, poultry and the like.

According to a further aspect of the invention, a method for controlling tumors in mammals, in particular man, is provided which is characterized in that at least one indole derivative of the general formula (1) is administered to a mammal in an amount effective for the treatment of the tumor. The therapeutically effective dose of the indole derivative according to the invention in question which is to be administered for the treatment depends inter alia on the nature and the stage of the oncosis, the age and the sex of the patient, the type of administration and the duration of the treatment. Administration can take place orally, rectally, buccally (for example sublingually), parenterally (for example subcutaneously, intramuscularly, intradermally or intravenously), topically or transdermally.

According to a further aspect of the invention, medicaments for the treatment of tumors are provided which are characterized in that they comprise, as active ingredient, at least one indole derivative according to any of claims 1 to 5 or a pharmaceutically acceptable salt thereof, if appropriate together with customary pharmaceutically acceptable auxiliaries, additives and carriers. These can be solid, semisolid, liquid or aerosol preparations. Suitable solid preparations are, for example, capsules, powders, granules, tablets. Suitable semisolid preparations are, for example, ointments, creams, gels, pastes, suspensions, oil-in-water and water-in-oil emulsions. Suitable liquid preparations are, for example, sterile aqueous preparations for parenteral administration which are isotonic with the blood of the patient.

The invention is to be illustrated in more detail by the example below, without being restricted to the example.

WORKING EXAMPLES

Example 1

Reaction According to Scheme 1, 1. Step

Preparation of 1-(4-chlorobenzyl)indole

A solution of 5.86 g (0.05 mol) of indole in 25 ml of DMSO is added to a mixture of 1.32 g of sodium hydroxide (0.055 mol, suspension in mineral oil) in 50 ml of dimethyl sulfoxide. The mixture is heated at 60° C. for 1.3 hours and then allowed to cool, and 17.7 g (0.11 mol) of 4-chlorobenzyl chloride are added dropwise. The solution is heated at 60° C., allowed to stand overnight and then poured with stirring into 200 ml of water. The mixture is extracted repeatedly with a total of 75 ml of $CH_2Cl_2$, the organic phase is dried with anhydrous sodium sulfate and filtered and the filtrate is concentrated under reduced pressure.

Yield: 11.5 g (95% of theory)

Example 2

Reaction According to the 2. Step of Scheme 1)

Preparation of N-(2-methyl-6-quinolyl)-[1-(4-chlorobenzyl)indole-3-yl]glyoxylamide (D69429)

At 0° C. and under nitrogen, a solution of 10.2 g (42.2 mmol) of 1-(4-chlorobenzyl)indole in 50 ml of ether is added dropwise to a solution of 5.50 ml of oxalyl chloride in 50 ml of ether. The mixture is heated at reflux for 2 hours and the solvent is then evaporated. 100 ml of tetrahydrofuran were then added to the residue and the solution was cooled to −4° C. and treated dropwise with a solution of 15.66 g (99.0 mmol) of 6-amino-2-methylquinoline in 350 ml of THF. The mixture is heated at reflux for 4 hours and allowed to stand at room temperature overnight. The 6-amino-2-methylquinoline hydrochloride is filtered off with suction, the precipitate is washed with THF, the filtrate is concentrated under reduced pressure and the residue is recrystallized from methyl ethyl ketone/methylene chloride.

Yield: 14.8 g (77.3% of theory)

Melting point: 182-185° C.

Synthesis of the Hydrochloride:

To a mixture of 0.453 g (1 mMol) N-(2-Methyl-6-quinolyl)-[1-(4-chlorobenzyl)-indol-3-yl]-glyoxylic acid amide in 20 ml hot ethanol is added under stirring the equivalent quantity of isopropanolic hydrochloric acid. The suspension is heated to 70-80° C. and the formed solution is evaporated to dryness under reduced pressure. The evaporating process is repeated several times with toluene to give the colorless and crystalline hydrochloride.

Yield: 0.49 g (100% of the theoretical)

Mp.: 196° C.

Synthesis of the Methansulfonate:

A mixture of 0.453 g (1 mMol) N-(2-Methyl-6-quinolyl)-[1-(4-chlorobenzyl)-indol-3-yl]-glyoxylic acid amide and 0.67 ml Methanesulfonic acid in 15 ml Dichloromethan is heated to 50° C. for 30 minutes. The so formed solution is concentrated und reduced pressure at 35° C. to dryness. The residue is evaporated several times with methyl-tert.-butylether, dried in the vacuo at 35° C. to provide the methansulfonate as white crystals.

Yield: 0.46 g (84% of the theoretical)

Mp.: >230° C.

Example 3

Reaction According to Scheme 3

Preparation of N-propargyl-N-(2-methyl-6-quinolyl)-[1-(4-chlorobenzyl)indol-3-yl]glyoxylamide At room temperature and under nitrogen, a suspension of 2.32 g (5.13 mmol) of N-(2-methyl-6-quinolyl))-[1-(4-chlorobenzyl)indol-3-yl]glyoxylamide in 20 ml of DMF is added to a suspension of 0.154 g of sodium hydride (5.13 mmol, suspension in mineral oil) in 10 ml of DMF. This resulted in strong foaming, with the mixture turning yellow. A solution of 0.382 g (5.13 mmol) of propargyl chloride in 10 ml of DMF is added dropwise, and the mixture is, under nitrogen gas, stirred at room temperature for 24 hours and allowed to stand at room temperature for 4 days. The dark-brown solution is then poured into 120 ml of ice water and extracted in portions with 250 ml of methylene chloride, and the combined organic phases are dried using anhydrous sodium sulfate. The extract is concentrated under reduced pressure and the residue is purified using a silica gel column (silica gel 60, from Merck AG, Darmstadt, Germany) and the mobile phase methylene chloride/ethanol (97:3, v/v).

Yield: 1.98 g (78.6% of theory)

Mass spectrum: m/e=491.9 ($M^+$)

Biological Tests

1. Antiproliferative Action in Various Tumor Cell Lines

In a proliferation test, the antiproliferative activity of the substance D-69429 was examined using established tumor cell lines. In the test used, the cellular dehydrogenation activity is determined, which makes it possible to determine the vitality of the cell and, indirectly, the cell count. The cell lines used are the human cervical carcinoma cell line KB/HeLa (ATCC CCL17), the murine lymphocyte a leukaemia L1210 (ATCC CCL-219), the human breast adenocarcinoma line MCF7 (ATCC HTB22) and the ovary adenocarcinoma line SKOV-3 (ATCC HTB77). These are established cell lines which are very well characterized and were obtained from ATCC and cultured.

Figure 1:
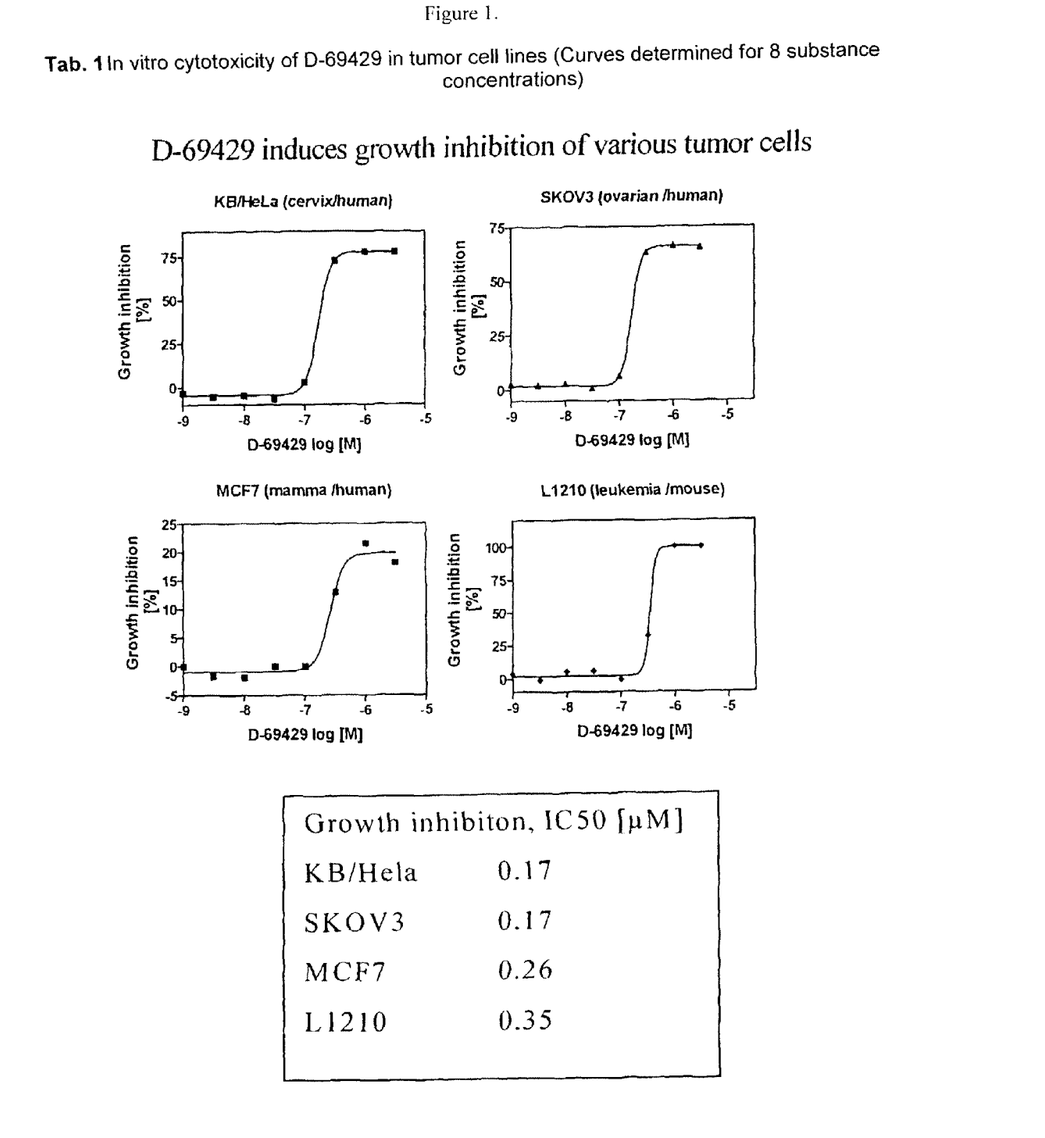
FIG. 1 shows graphs of in vitro cytotoxicity of D-69429 in tumor cell lines for 8 substance concentrations.

The results shown in Tab. 1 of FIG. 1 demonstrate the highly potent antiproliferative action of D-69429 in the cell lines SKOV-3, L-1210 and HeLa/KB for eight (8) substance concentrations. Owing to the particularly slow growth of the MCF7 line, the effect of D-69429 in the test period of 48 h is only small (18% inhibition at 3.16 μg/ml; thus stated as >3.16).

2. Method

XTT Test for Cellular Dehydrogenase Activity

The adherently growing tumor cell lines HeLa/KB, SKOV-3 and MCF7 and the L1210 leukaemia line, which grows in suspension, were cultivated under standard conditions in an incubator with gas inlet at 37° C., 5% $CO_2$ and 95% atmospheric humidity. On Test Day 1, the adherent cells are detached using trypsin/EDTA and pelleted by centrifugation. The cell pellet is then resuspended in the RPMI culture medium at the appropriate cell count and transferred to a 96-well microtiter plate.

The plates are then cultivated overnight in the incubator with gas inlet. The test substances are made up as stock solutions in DMSO and, on Test Day 2, diluted with culture medium to the corresponding concentrations. The substances in the culture medium are then added to the cells and incubated in the incubator with gas inlet for 45 h. Cells which have, not been treated with test substance serve as control.

For the XTT assay, 1 mg/ml of XTT (sodium 3'-[1-(phenylaminocarbonyl)-3,4-tetrazolium]-bis(4-methoxy-6-nitro) benzenesulfonic acid) is dissolved in RPMI-1640 medium without Phenol Red. Additionally, a 0.383 mg/ml solution of PMS (N-methyldibenzopyrazine methyl sulfate) in phosphate-buffered saline (PBS) is prepared. On Test Day 4, 75 µl/well of the XTT-PMS mixture are pipetted onto the cell plates, which by now have been incubated with the test substances for 45 h. To this end, the XTT solution is mixed with the PMS solution in a ratio of 50:1 (v/v) shortly before use. The cell plates are then incubated in the incubator with gas inlet for a further 3 h, and the optical density ($OD_{490nm}$) is determined in a photometer.

Using the $OD_{490nm}$ obtained, the inhibition in percent relative to the control is calculated. The antiproliferative activity is estimated using regression analysis.

Example I

Tablet containing 50 mg of active compound
Composition:

| | | |
|---|---|---|
| (1) | Active compound | 50.0 mg |
| (2) | Lactose | 98.0 mg |
| (3) | Maize starch | 50.0 mg |
| (4) | Polyvinylpyrrolidone | 15.0 mg |
| (5) | Magnesium stearate | 2.0 mg |
| | Total: | 215.0 mg |

Preparation:

(1), (2) and (3) are mixed and granulated with an aqueous solution of (4). The dried granules are admixed with (5). This mixture is tabletted.

Example II

Capsule containing 50 mg of active compound
Composition:

| | | |
|---|---|---|
| (1) | Active compound | 50.0 mg |
| (2) | Maize starch, dried | 58.0 mg |
| (3) | Lactose powder | 50.0 mg |
| (4) | Magnesium stearate | 2.0 mg |
| | Total: | 160.0 mg |

Preparation:

(1) is ground with (3): This ground material is added with vigorous mixing to the mixture of (2) and (4). This powder mixture is, on a capsule filling machine, filled into hard gelatine capsules size 3.

What is claimed:

1. Indole compounds of the general Formula 1

Formula 1 in which

R denotes hydrogen, straight-chain ($C_1$-$C_6$)-alkyl or branched ($C_1$-$C_6$)-alkyl;

$R_1$ denotes a 5-quinolyl, 6-quinolyl or 7-quinolyl group bonded to the amide nitrogen directly:

$R_2$ denotes hydrogen-$o_2$($C_1$-$C_6$)-alkyl, or ($C_1$-$C_6$)-alkyl which is mono- or polysubstituted by phenyl, where the phenyl radical may be unsubstituted or mono- to penta-substituted by identical or different substituents from the group consisting of halogen, preferably chlorine, bromine or iodine;

$R_3$ and $R_4$ may be attached to the indole carbon atoms C-2, C-4, C5, C-6 or C-7 and independently of one another denote hydrogen, hydroxyl, ($C_1$-$C_6$)-alkyl, ($C_3$-$C_7$)-cycloalkyl, ($C_1$-$C_6$)-alkylcarbonyl, ($C_1$-$C_6$)-alkoxy, halogen, aryl-($C_1$-$C_4$)-alkoxy, nitro, amino, mono-($C_1$-$C_4$)-alkylamino, di-($C_1$-$C_4$)-alkylamino, ($C_1$-$C_6$)-alkoxycarbonylamino, ($C_1$-$C_6$)-alkoxycarbonylamino-($C_1$-$C_6$)-alkyl, cyano, straight-chain or branched cyano-($C_1$-$C_6$)-alkyl, carboxyl, ($C_1$-$C_4$)-alkoxycarbonyl, ($C_1$-$C_4$)-alkyl which is substituted by one or more fluorine atoms, carboxy-($C_1$-$C_6$)-alkyl or ($C_1$-$C_6$)-alkoxycarbonyl-($C_1$-$C_6$)-alkyl;

$Z_1$ denotes oxygen or sulfur;

$Z_2$ denotes oxygen or sulfur.

2. Indol compound according to claim 1 characterized in that R, $R_1$, $R_2$, $Z_1$ and $Z_2$ have the meanings described above and $R_3$ and $R_4$ each denote hydrogen.

3. Indole compound as in claim 1, characterized in that R, $R_1$, $R_2$, $R_3$ and $R_4$ have the meanings described above and $Z_1$ and $Z_2$ each denote oxygen.

4. Indole compound as in claim 2, characterized in that R, $R_1$, $R_2$, $R_3$ and $R_4$ have the meanings described above and $Z_1$ and $Z_2$ each denote oxygen.

5. Indole compound as in any of claims 1, 3 and 4, characterized in that R, $R_1$, $R_3$, $R_4$, $Z_1$ and $Z_2$ have the meanings described above and $R_2$ denotes chlorobenzyl.

6. Indole compound as in any of claims 1, 3 and 4, characterized in that R, $R_2$, $R_3$, $R_4$, $Z_1$ and $Z_2$ have the meanings described above and $R_1$ denotes 6-quinolinyl.

7. Indole compound according to claim 1 characterized in that R denotes hydrogen, $R_1$ denotes 6-quinolinyl, $R_2$ denotes chlorobenzyl, $R_3$ and $R_4$ each denote hydrogen and $Z_1$ and $Z_2$ each denote oxygen.

8. Process for preparing indole compounds of the general formula (1) as in any of claims 1, 3, 7 and 4, characterized in that an indole precursor of the general formula (2)

Formula 2 in which $R_2$, $R_3$ and $R_4$ have the meanings mentioned above is reacted with a compound of the general formula (3)

Formula 3 in which $Z_1$ and $Z_2$ have the meaning mentioned above and $Y_1$ and $Y_2$ independently of one another represent a suitable leaving group, such as halogen, $(C_1$-$C_6)$-alkoxy, —O-tosyl, —O-mesyl or —N1-imidazole, and then with an amine of the general formula (4) or (5)

Formula 4

Formula 5 in which R and $R_1$ have the meanings mentioned above, giving the desired compound of the general formula (1)(with amine 4) or the compound of the general formula (6)(with amine 5)

Formula 6 in which $R_1$, $R_2$, $R_3$, $R_4$, $Z_1$ and $Z_2$ have the meanings mentioned above, using, if appropriate, diluents and auxiliaries, where the compound of the general formula (6) may subsequently be reacted with a compound of the general formula (7)

$$R-Y_3 \quad (7)$$

in which R has the meaning mentioned above and $Y_3$ represents a suitable electrophilic leaving group, such as halogen, $(C_1$-$C_6)$-alkoxy, —O-tosyl, —O-mesyl or N1-imidazole, giving the desired compound (1), where R does not denote hydrogen, using, if appropriate, diluents and auxiliaries.

9. Method for treating tumors in mammals, characterized in that at least one indole compound of the general formula (1) as in any of claims 1, 3, 7 and 4, is administered to the mammal in a dose effective for tumor treatment.

10. Medicament, characterized in that it comprises, as active ingredient, at least one indole compound of the general formula (1) as in any of claims 1, 3, 7 and 4, if appropriate together with customary pharmaceutically acceptable auxiliaries, additives and carriers.

11. Indole compound as in any of claims 3 and 4, characterized in that $R_1$, $R_2$, $R_3$, $R_4$, $Z_1$ and $Z_2$ have the meanings described above and R denotes hydrogen.

\* \* \* \* \*